United States Patent [19]
Uchiyama et al.

[11] Patent Number: 4,898,574
[45] Date of Patent: Feb. 6, 1990

[54] LITHOTOMIC APPARATUS

[75] Inventors: Naoki Uchiyama, Tokyo; Yoshio Shishido, Sagamihara; Yasuhiro Ueda, Tokyo, all of Japan

[73] Assignee: Olympus Optical Co., Ltd., Tokyo, Japan

[21] Appl. No.: 306,267

[22] Filed: Feb. 1, 1989

Related U.S. Application Data

[63] Continuation of Ser. No. 45,127, Apr. 30, 1987, abandoned.

[30] Foreign Application Priority Data

May 8, 1986 [JP] Japan .................. 61-105292
May 8, 1986 [JP] Japan .................. 61-105295
May 8, 1986 [JP] Japan .................. 61-105296
Jul. 24, 1986 [JP] Japan .................. 61-174318

[51] Int. Cl.$^4$ ........................... A61B 17/22
[52] U.S. Cl. ........................... 604/22; 606/127
[58] Field of Search ............... 128/328, 24 A; 604/22

[56] References Cited

U.S. PATENT DOCUMENTS 3,413,976 12/1968 Roze .
3,863,628 2/1975 Vit .......................... 433/88
3,886,933 6/1975 Mori et al. .............. 128/328 X
4,690,672 9/1987 Veltrup .................... 604/43

FOREIGN PATENT DOCUMENTS 1218112 of 0000 Fed. Rep. of Germany .
3019115 5/1985 Fed. Rep. of Germany .
3421390 12/1985 Fed. Rep. of Germany ...... 128/305
3438131 4/1986 Fed. Rep. of Germany ...... 128/328
464799 of 0000 Japan .
6168035 of 0000 Japan .
59225049 of 0000 Japan .
60193452 of 0000 Japan .
60195008 of 0000 Japan .
60192808 7/1982 Japan .
8103125 11/1981 World Int. Prop. O. ............ 604/22

OTHER PUBLICATIONS

Search Report.

Primary Examiner—Michael H. Thaler
Attorney, Agent, or Firm—Ladas & Parry

[57] ABSTRACT

A lithotomic apparatus includes a probe for insertion into the body cavity. A distal tip is fixed to the distal end of the probe and has nozzles. Each nozzle has a rear end communicating with a feed passage defined in the probe and a front end opening to the distal end face of the distal tip. A high-pressure fluid supplied from a source is fed to the feed passage of the probe and pulsatively ejected from the nozzles toward a calculus in the body cavity by a drive mechanism.

7 Claims, 10 Drawing Sheets

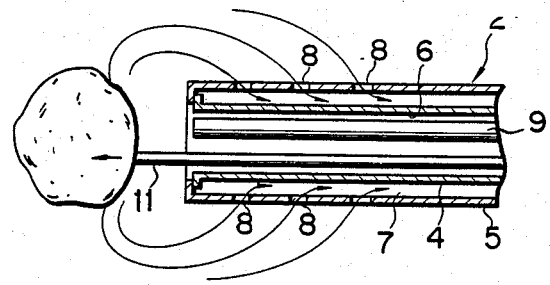
F I G. 2
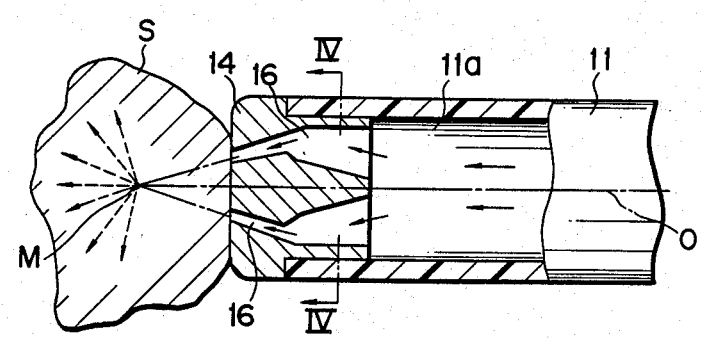
F I G. 3
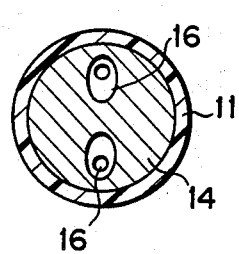
F I G. 4
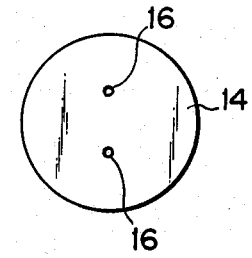
F I G. 5

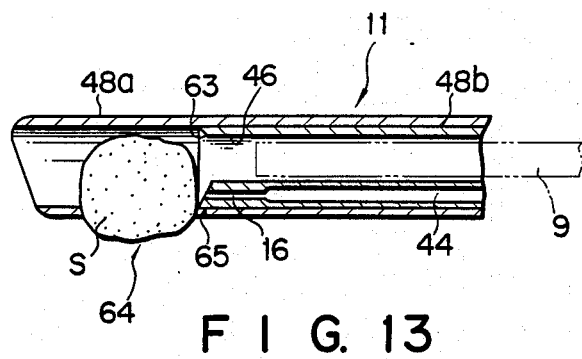
F I G. 13
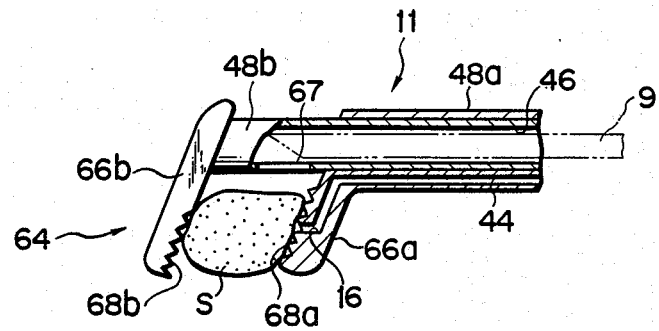
F I G. 14
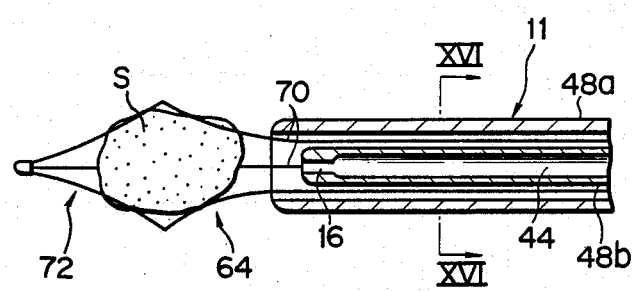
F I G. 15

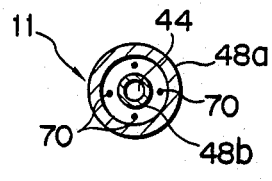
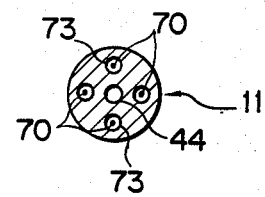
F I G. 16        F I G. 17
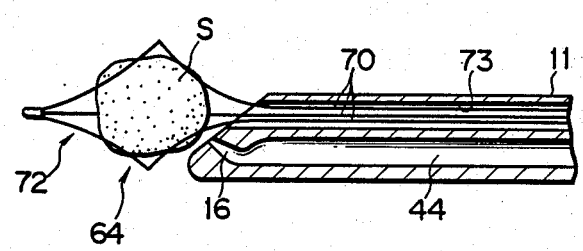
F I G. 18
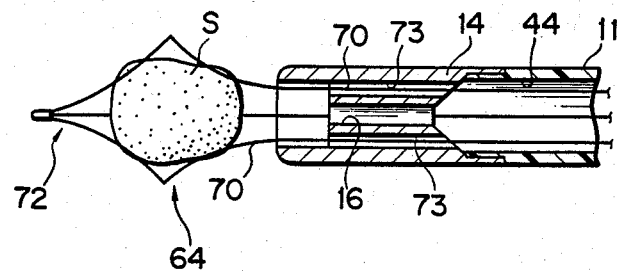
F I G. 19

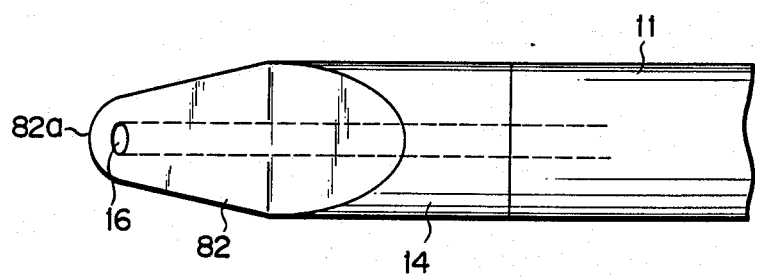
F I G. 26
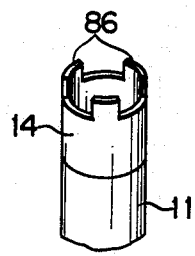 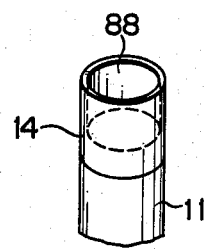 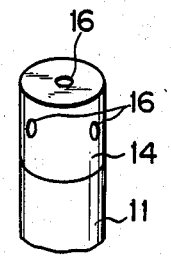
F I G. 27    F I G. 28    F I G. 29
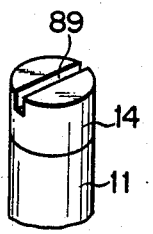 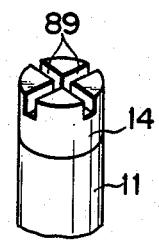 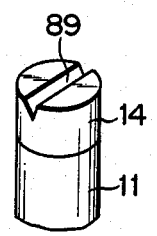
F I G. 30    F I G. 31    F I G. 32 ns. 4,898,574

LITHOTOMIC APPARATUS

This is a continuation of co-pending application Ser. No. 045,127 filed on Apr. 30, 1987, now abandoned.

BACKGROUND OF THE INVENTION

The present invention relates to a lithotomic apparatus for desired lithotomic operations, such as crushing of a calculus in the body cavity, separation of a calculus adhering to the tissues of a patient's body, etc.

Various apparatuses have conventionally been provided which destroy a calculus produced in a hollow or cavity of a kidney, ureter, or some other internal organ. One such prior art apparatus is designed so as to crush a calculus by means of a laser beam emitted from a laser probe. With use of this apparatus, however, the laser beam is applied to the body wall, thereby injuring it.

Stated in Japanese Patent Disclosure No. 60-192808 is an apparatus which incises or removes the tissues of the human body by means of a high-pressure fluid. Although not disclosed in the Japanese Patent Disclosure, it may be possible to think of an arrangement in which a calculus is crushed or separated by means of a pressurized fluid. In crushing a calculus with use of a high-pressure fluid, however, the pressure of the fluid must be made higher than that in the case of treating the body tissues. Thus, the high-pressure fluid, like the laser beam, is very likely to injure the body wall.

SUMMARY OF THE INVENTION

The present invention has been contrived in consideration of these circumstances, and is intended to provide a lithotomic apparatus capable of treating a calculus by means of a high-pressure fluid, without injuring the body wall.

In order to achieve the above object, a lithotomic apparatus according to the present invention comprises an elongated probe having a nozzle portion at the distal end thereof and adapted to be inserted into the body cavity, a source for supplying a high-pressure fluid, and a drive mechanism for controlling the high-pressure fluid so that the fluid is jetted pulsatively from the nozzle portion.

According to the lithotomic apparatus described above, the high-pressure fluid is jetted pulsatively, so that it cannot be dashed continuously against one spot on the body wall. Thus, a calculus can be treated without injuring the body wall.

BRIEF DESCRIPTION OF THE DRAWINGS

FIGS. 1 to 5 show a lithotomic apparatus according to a first embodiment of the present invention, in which FIG. 1 is a view showing an outline of the apparatus; FIG. 2 is a cutaway side view showing the distal end portion of an insertion section of an endoscope and the distal end portion of a probe of the lithotomic apparatus, FIG. 3 is an enlarged sectional view of the probe end portion, FIG. 4 is a sectional view taken along line IV—IV of FIG. 3, and FIG. 5 is a front view of the tip end face of the probe;

FIGS. 8 to 11 show a lithotomic apparatus according to a second embodiment of the invention, in which FIG. 8 is an enlarged sectional view showing the distal end portion of a probe of the apparatus, FIG. 9 is a sectional view taken along line IX—IX of FIG. 8, FIG. 10 is a sectional view taken along line X—X of FIG. 8, and FIG. 11 is a front view of the front end face of the probe;

FIGS. 12 and 13 show a lithotomic apparatus according to a third embodiment of the invention, in which FIG. 12 is a side view showing an outline of the apparatus, and FIG. 13 is a sectional view showing the distal end portion of a probe;

FIG. 14 is a sectional view showing the distal end portion of a probe of a lithotomic apparatus according to a fourth embodiment of the invention;

FIGS. 15 and 16 show a lithotomic apparatus according to a fifth embodiment of the invention, in which FIG. 15 is a sectional view showing the distal end portion of a probe, and FIG. 16 is a sectional view taken along line XVI—XVI of FIG. 15;

FIGS. 17, 18 and 19 are sectional views showing first, second, and third modifications of the fifth embodiment, respectively;

FIGS. 25 and 26 are a sectional view and a plan view, respectively, showing a second modification of the seventh embodiment;

FIGS. 27 to 32 are perspective views showing different modifications of a distal tip;

FIGS. 34 and 35 show a lithotomic apparatus according to an eighth embodiment of the invention, in which FIG. 34 is a schematic view showing the distal end portion of a probe, and FIG. 35 is a schematic view illustrating an operation for crushing a calculus.

DETAILED DESCRIPTION OF THE PREFERRED EMBODIMENTS

Embodiments of the present invention will now be described in detail with reference to the accompanying drawings.

Figure 1:
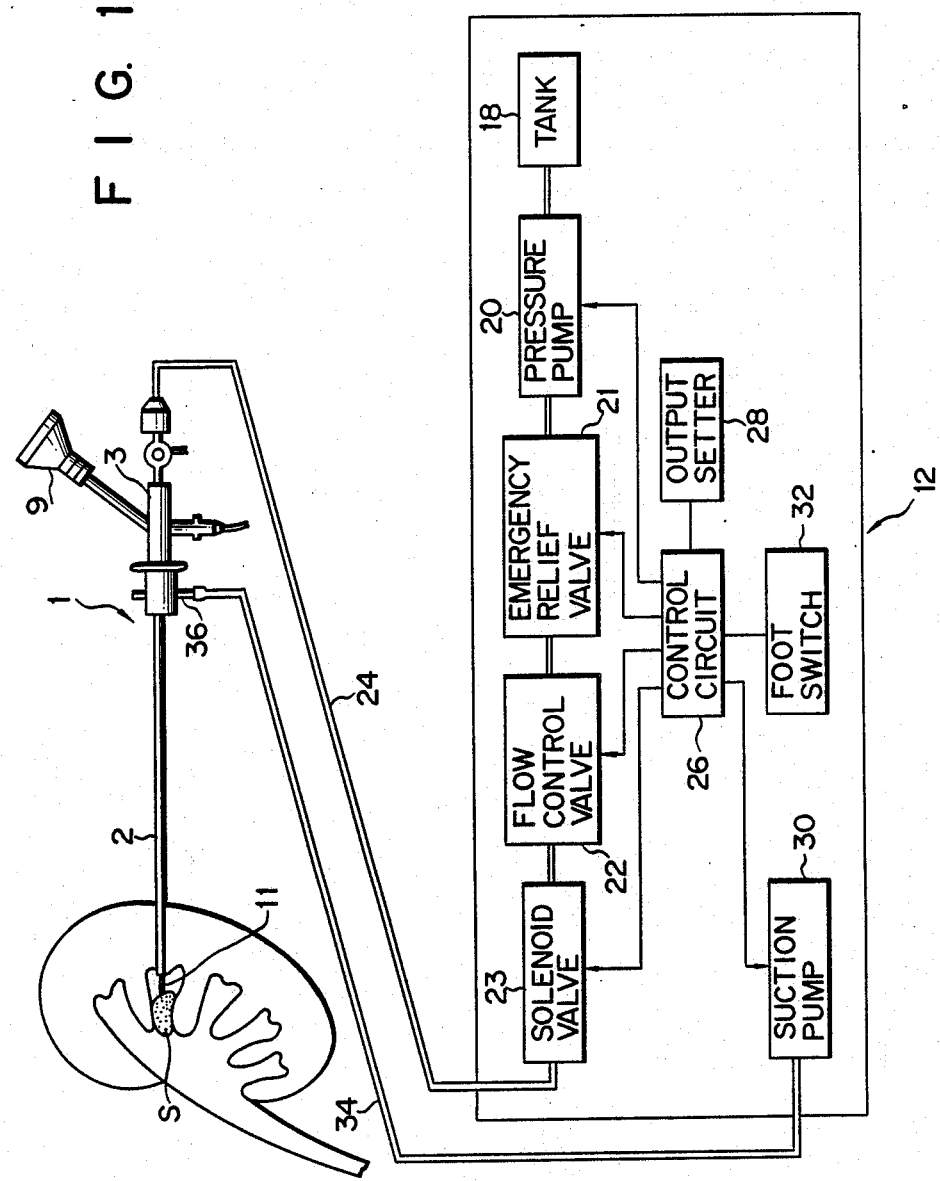

FIG. 1 shows a lithotomic apparatus according to a first embodiment of the present invention, which is inserted in a hollow or cavity of an internal organ by means of endoscope 1. As is shown in FIGS. 1 and 2, endoscope 1 comprises operation section 3 and insertion section 2. Section 2, which extends from section 3, is inserted in the cavity. The insertion section has a double-tube structure, including inner and outer tubes 4 and 5. Inner tube 4 defines therein instrument channel 6, and suction channel 7 is defined between the inner and outer tubes. The outer peripheral wall of outer tube 5, is formed, at the distal end portion thereof, with a plurality of suction holes 8 which communicate with suction channel 7.

The lithotomic apparatus comprises elongated flexible probe 11, which, along with optical view tube 9, is passed through instrument channel 6 of endoscope 1, and drive unit 12 connected to the proximal end of the probe and used to supply a pressurized fluid thereto. As is shown in FIGS. 3 to 5, probe 11 includes a tube whose inner peripheral surface defines feed passage 11a. Distal tip 14, which is formed of metal or rigid plastic material, is fixed to the distal end of probe 11. It serves as a nozzle portion. A pair of nozzles 16 are bored through tip 14. Each nozzle 16 has a rear end, which opens to the rear end face of tip 14 and communicates with passage 11a of probe 11, and a front end which opens to the front end face of the tip. Nozzle 16 is gradually reduced in its cross-sectional area progressing from its rear end. The two nozzles are arranged symmetrically with respect to central axis 0 of probe 11. Also, nozzles 16 extend aslant toward axis 0 of probe 11 so that extensions of their respective axes intersect at point M, which is situated a predetermined distance ahead of the front end face of tip 14. Thus, jets of the pressurized fluid, spouted from nozzles 16, collide against each other at point M, thereby scattering, as described in detail later.

As is shown in FIG. 1, drive unit 12 includes tank 18 and pressure pump 20. Tank 18 is stored with a fluid, such as a physiological saline solution or adrenalin. Pump 20 serves as a source of supply whereby the fluid in the tank is pressurized and fed to probe 11. Emergency relief valve 21, flow control valve 22, and solenoid valve 23 are connected successively to the discharge side of pump 20. Valve 23 is connected to the proximal end of probe 11, or that of feed passage 11a, by means of first tube 24. Pressure pump 20 and valves 21 to 23 are electrically connected to control circuit 26. Also, output setter 28, suction pump 30, and foot switch 32 are electrically connected to circuit 26.

Output setter 28 is used to set the maximum flow rate (pressure) of the fluid flowing through flow control valve 22. If the high-pressure fluid flows through valve 22 at a flow rate higher than the maximum flow rate, relief valve 21 is closed by control circuit 26. As a result, the fluid is prevented from being supplied from first tube 24 to probe 11. Solenoid valve 23 is intermittently on-off controlled by the control circuit. The pitch of the on-off operation of valve 23 is set as required. Thus, the high-pressure fluid is fed pulsatively to probe 11 at predetermined time intervals. When foot switch 32 is worked, pressure pump 20 is actuated to supply the fluid to probe 11. When switch 32 is turned off, the fluid supply is stopped.

Suction pump 30 is connected, by means of second tube 34, to mouthpiece 36 which is attached to operation section 3 of endoscope 1. Mouthpiece 36 communicates with suction channel 7 of insertion section 2. Thus, when suction pump 30 is actuated by control circuit 26, a negative pressure is produced inside the suction channel. Control circuit 26 controls pump 30 in a manner such that the negative pressure in suction channel 7 is higher when solenoid valve 23 is turned on, thereby allowing the high-pressure fluid to spout from probe 11, than when valve 23 is turned off to keep the fluid from spouting from the probe.

In crushing calculus S in a kidney, for example, by using the lithotomic apparatus constructed in this manner, control circuit 26 is first driven to set the maximum flow rate of flow control valve 22 and the pitch of the intermittent operation of solenoid valve 23. Then, insertion section 2 of endoscope 1 is inserted into the kidney, and optical view tube 9 and probe 11 are inserted into a cavity in the kidney, through instrument channel 6 of the endoscope. Using view tube 9 for observation, as shown in FIG. 2 and 3, the distal end face of distal tip 14 of probe 11 is brought close to calculus S. In this state, foot switch 32 is turned on to actuate pressure pump 20. Thereupon, the fluid in the tank 18 is pressurized and supplied to feed passage 11a of probe 11 via the valves and first tube 24. The high-pressure fluid is discharged from nozzles 16 of distal tip 14 toward calculus S, thereby crushing it. In doing this, the fluid is spouted pulsatively from nozzles 16 in association with the on-off operation of solenoid valve 23. Since each nozzle 16 is tapered toward its front end, the pressurized fluid increases its flowing speed as it passes through the nozzle. Thus, a sufficient destructive force can be applied to the calculus to destroy it.

The moment pressure pump 20 is actuated, suction pump 30 also starts to work. Accordingly, a negative pressure is produced inside suction channel 7 of insertion section 2. Thus, after spouting from nozzles 16 to crush calculus S, the high-pressure fluid is sucked into channel 7 through suction holes 8. The negative pressure inside suction channel 7 is controlled so that it is higher while the fluid is spouting from nozzles 16. Therefore, the high-pressure fluid jetted from probe 11 cannot injure a patient's body, since the fluid does not remain in the hollow or cavity of the kidney, for example. Also, the crushed calculus, along with high-pressure air, can be removed from the cavity by being sucked into suction channel 7.

Constructed in this manner, the lithotomic apparatus of this embodiment has the following advantages.

In crushing calculus S, the high-pressure fluid jetted from probe 11 may sometimes be splashed on the body wall by mistake. According to the apparatus described above, however, the fluid is jetted pulsatively under the control by solenoid valve 23. Therefore, the high-pressure fluid cannot be dashed continuously against one spot on the body wall, preventing injury to the body wall. When calculus S is crushed and removed from the region in front of distal tip 14, the jets of the fluid ejected from paired nozzles 16 collide against each other at point M, and then scatter in all directions. After the calculus crushing, therefore, the fluid can never be dashed against the body wall under a high-pressure condition. Thus, the body cavity can be prevented more securely from being injured by the fluid.

Figure 6:
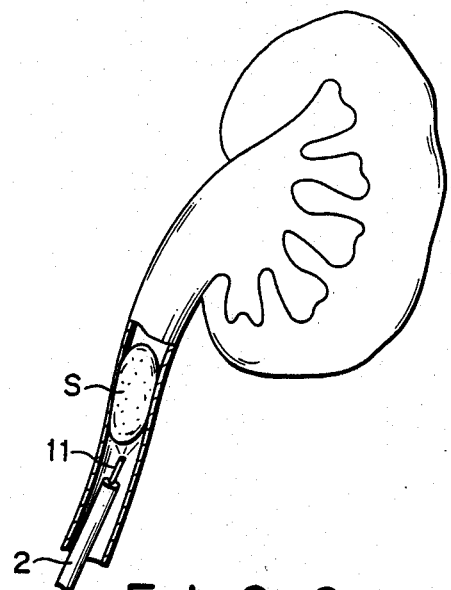
FIGS. 6 and 7 are views schematically illustrating different ways of using the apparatus shown in FIGS. 1 to 5.
Figure 7:
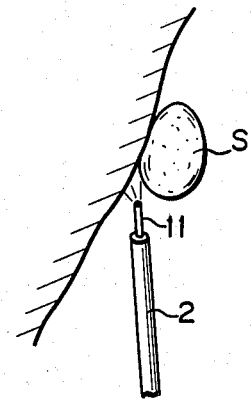
Figure 8:
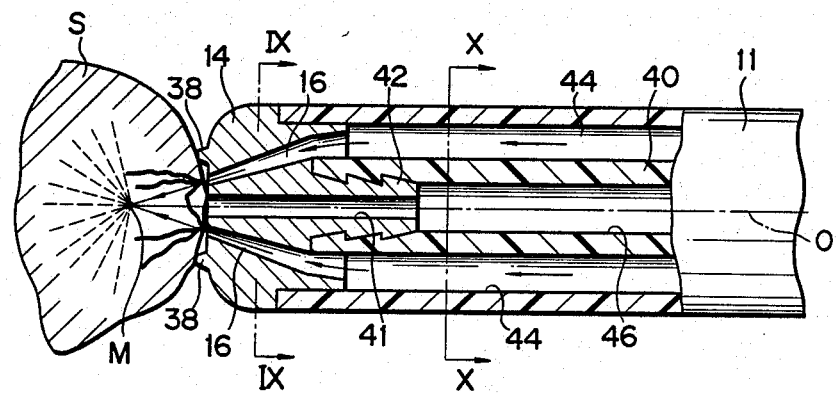
Figure 9:
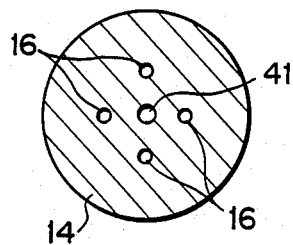
Figure 10:
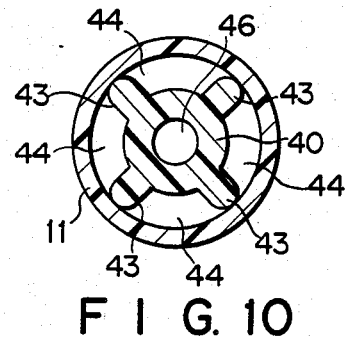
Figure 11:
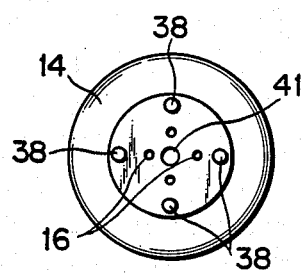

Also, the body wall can be prevented from being injured by the high-pressure fluid, jetted from probe 11, when transferring calculus S from a ureter to a kidney, as is shown in FIG. 6, or when separating adherent calculus S from the tissues of the patient's body, as is shown in FIG. 7, by means of the pressurized fluid.

In the first embodiment, the negative pressure produced in the suction channel may be controlled so that it is higher when solenoid valve 23 is turned off to keep the high-pressure fluid from spouting. In this case, the fluid jetted from probe 11 can never be sucked into suction channel 7 before it dashes against calculus S.

FIGS. 8, 9, 10 and 11 show a second embodiment of the present invention.

According to the second embodiment, four projections 38 are formed on the distal end face of distal tip 14. Calculus S can be held securely between tip 14 and the body wall by pressing projections 38 against the calculus. Also, four nozzles 16 are bored through distal tip 14. They are arranged at regular intervals along the circumference of a circle around central axis 0 of probe 11. Nozzles 16 extend aslant so that their respective central axes intersect one another at point M in front of distal tip 14. Tip 14 is formed further with suction hole 41 which extends coaxially with probe 11.

Cylindrical partition member 40 is passed through probe 11. The distal end of member 40 is coupled to connecting portion 42 which is formed on the rear end face of distal tip 14. Partition member 40 has four ribs 43 protruding radially from its outer peripheral surface and extending over the full length thereof. The top of each rib 43 is in contact with the inner peripheral surface of probe 11. Thus, the inside space of probe 11 is divided into four feed passages 44 by the partition member. These feed passages communicate with their corresponding nozzles 16. Suction channel 46 is defined by the inner peripheral surface of partition member 40. The distal and proximal ends of channel 46 communicate with suction hole 41 and the suction pump (FIG. 1), respectively.

Except for these arrangements, the second embodiment has the same construction as the first embodiment. According to the second embodiment constructed in this manner, a high-pressure fluid, fed pulsatively from the drive unit, flows through feed passages 44, and is jetted substantially uniformly from four nozzles 16. Thereupon, calculus S is crushed by the spouting fluid. As in the case of the first embodiment, the high-pressure fluid is jetted pulsatively, and the jets of the fluid collide against one another and then scatter at point M. Thus, the body wall can be prevented from being injured by the high-pressure fluid.

Moreover, calculus S can be sucked and fixed securely to distal tip 14 by actuating the suction pump to produce a negative pressure in suction channel 46 and suction hole 41. Also, the crushed calculus can be removed from the cavity through section hole 41 by suction.

In the second embodiment, the sucking force may be produced by connecting one of feed passages 44 to the suction pump, instead of using suction channel 46 and suction hole 41.

Figure 12:
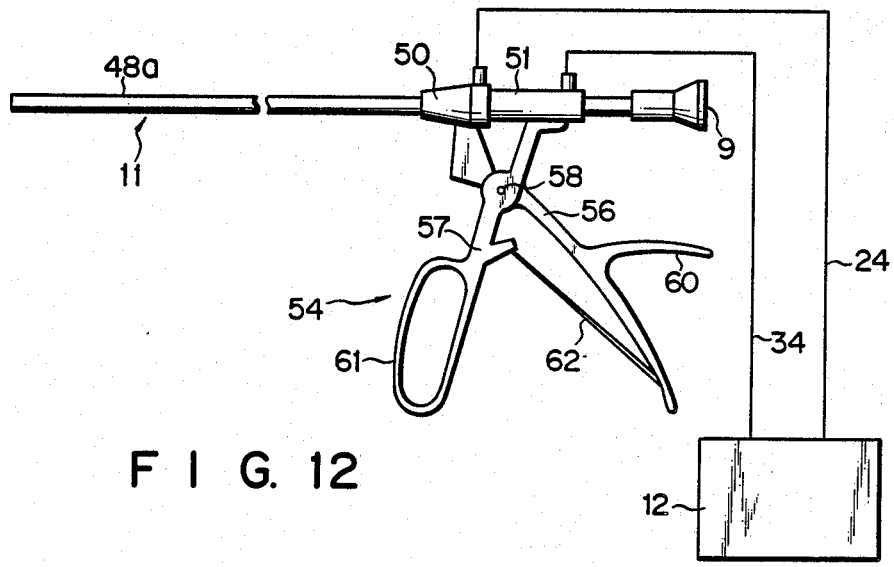

FIGS. 12 and 13 show a third embodiment of the present invention.

In crushing the calculus, it may sometimes be driven away from probe 11 by the pressure of the high-pressure fluid jetted from the nozzles. Thereupon, a lithotomic apparatus according to the third embodiment comprises a retaining mechanism for holding the calculus in the vicinity of the nozzles.

As is shown in FIGS. 12 and 13, probe 11 includes outer tube 48a and inner tube 48b slidably passed through the outer tube. First and second mouthpieces and 51 are fixed to the rear ends of tubes 48a and 48b respectively. Mouthpiece 50 and 51 slidably engage each other. One end of each of the first and second levers 56 and 57 of operating mechanism 54 are connected to first and second mouthpieces 50 and 51, respectively. The respective middle portions of levers 56 and 57 are rockably connected to each other by means of pivot 58. First and second handle portions 60 and 61 are formed at the other ends of levers 56 and 57, respectively. Spring 62 is anchored between levers 56 and 57 so as to urge the respective other end portions of the levers to separate from each other. Thus, if the other end portions of levers 56 and 57 are urged to approach each other, against the urging force of spring 62, inner tube 48b slides forward in outer tube 48a.

When first and second levers 56 and 57 are separated, the distal end portion of outer tube 48a extends forwardly beyond the distal end of inner tube 48b. The distal end face of inner tube 48b constitutes tapered surface 63 having a sharp end edge. Aperture 65 is bored through the distal end portion of the peripheral wall of outer tube 48a. Tapered surface 63 and aperture 65 constitute retaining mechanism 64. Inner tube 48b is formed with feed passage 44 and suction channel 46 which extend over the full axial length of tube 48b. The front end of feed passage 44 communicates with nozzle 16 which opens to tapered surface 63 of inner tube 48b. The rear end of passage 44 communicates with one end of first tube 24, at the location of second mouthpiece 51. The other end of tube 24 is connected to drive unit 12. Thus, when drive unit 12 is operated, the high-pressure fluid, produced thereby, passes through tube 24 and passage 44, and spouts pulsatively from nozzle 16. One end of second tube 34 is connected to mouthpiece 51 of tube 48b and communicates with suction channel 46 of inner tube 48b. The other end of tube 34 is connected to the suction pump (FIG. 1) of drive unit 12. When the suction pump is actuated by unit 12, a negative pressure is produced in suction channel 46 of inner tube 48b. Optical view tube 9, whose outside diameter is smaller than the inside diameter of channel 46, is passed through channel 46.

In crushing calculus S in the body cavity by the use of the lithotomic apparatus with the aforementioned construction, probe 11 is first inserted into the cavity. Then, the distal end of probe 11 is brought close to calculus S under observation through optical view tube 9, whereupon the calculus is taken into aperture 65 in outer tube 48a. Thereafter, first and second levers 56 and 57 are urged so as to approach each other, so that inner tube 48b in outer tube 48a is advanced relatively thereto. Thus, as is shown in FIG. 13, calculus S in aperture 65 is held between the inner peripheral edge of aperture 65 and tapered surface 63 of inner tube 48b. In this state, drive unit 12 is actuated to cause the high-pressure fluid to spout pulsatively from nozzle 16. Thereupon, the fluid acts securely on calculus S, thereby crushing it. At the same time, the suction pump is actuated. Thus, calculus S is not only crushed by the high-pressure fluid, but also sucked into suction channel 46.

According to the third embodiment constructed in this manner, calculus S can be crushed securely by being held in a position facing nozzle 16. As in the foregoing embodiments, moreover, the high-pressure fluid is jetted pulsatively, so that the calculus can be removed without injuring the body wall.

According to a fourth embodiment shown in FIG. 14, L inner tube 48b of probe 11 projects beyond the distal end of outer tube 48a. First clamping member 66a protrudes in a direction transverse to the axis of probe 11, from the peripheral surface of the distal end portion of outer tube 48a. Second clamping member 66b protrudes parallel to first member 66a from the distal end of inner tube 48b. Rugged surfaces 68a and 68b are formed on opposite faces of clamping members 66a and 66b respectively. Members 66a and 66b constitute retaining mechanism 64 for holding calculus S in position. Feed passage 44 is formed in outer tube 48a, and nozzle 16, which communicates with the distal end of the feed passage, opens to rugged surface 68a of first clamping member 66a. The peripheral wall of inner tube 48b has aperture 67 situated between clamping members 66a and 66b. Thus, the state of calculus S can be observed through optical view tube 9 inserted in suction channel 46 of tubechannel 46 of tube 48b.

According to the lithotomic apparatus constructed in this manner, calculus S can be clamped between members 66a and 66b and can be crushed securely by means of a high-pressure fluid jetted pulsatively from nozzle 16.

As is shown in FIGS. 15 and 16, retaining mechanism 64 may be constructed by a plurality of wires 70 and a basket 72 coupled thereto. According to this fifth embodiment, feed passage 44 and nozzle 16 are formed in inner tube 48a. Wires 70 are passed between inner and outer tubes 48b and 48a, and basket 72 is coupled to the respective distal ends of the wires, so as to be situated in front of nozzle 16.

After calculus S is taken into basket 72 projecting forward from outer tube 48a, wires 70 are manipulated to draw the basket into the distal end portion of tube 48a. Thus, calculus S can be held in a position facing nozzle 16. In this state, it can be crushed securely by pulsatively jetting a high-pressure fluid from nozzle 16.

In the fifth embodiment described above, probe 11 may be formed of a solid rod-shaped member which has feed passage 44 and a plurality of apertures 73 through which wires 70 are passed, as is shown in FIG. 17.

As is shown in FIG. 18, moreover, solid probe 11 may be formed with feed passage 46 and aperture 73 for the passage of wires 70, the feed passage and the aperture extending parallel to each other. In this case, nozzle 16, which communicates with the feed passage and opens to the distal end face of probe 11, extends aslant toward basket 72.

As is shown in FIG. 19, furthermore, distal tip 14, which is formed with nozzle 16 and a plurality of apertures 73 for the passage of wires 70, may be fixed to the distal end of hollow cylindrical probe 11.

Figure 20:
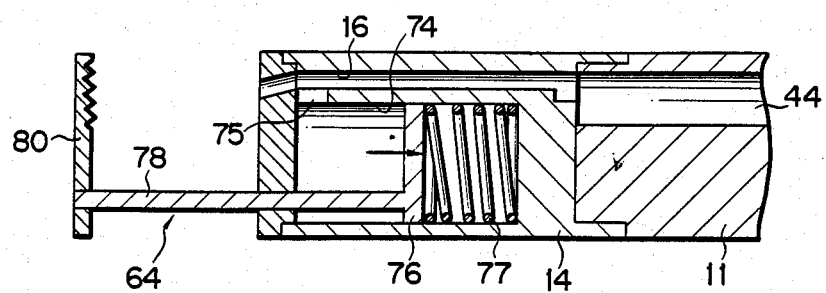
FIG. 20 is a sectional view showing the distal end portion of a probe of a lithotomic apparatus according to a sixth embodiment of the invention.

FIG. 20 shows a sixth embodiment of the present invention. According to this embodiment, distal tip 14 is fixed to the distal end of probe 11 which has feed passage 44 therein. Tip 14 is formed with nozzle 16 which communicates with passage 44 and opens to the distal end face of tip 14. Also, cylindrical chamber 74, extending along the axial direction of probe 11, is defined in tip 14. Chamber 74 communicates with nozzle 16 by means of communication hole 75. Slider 76 and spring 78 are arranged in chamber 74. Slider 76 is slidable along the axial direction of probe 11, and spring 77 urges the slider forward, with respect to the probe. Rod 78, which is fixed to slider 76, penetrates tip 14 and projects forward from the distal end face thereof. Backup plate 80 is fixed to the projecting end of rod 78 so as to face the distal end face of tip 14.

According to the sixth embodiment constructed in this manner, when a high-pressure fluid is supplied to feed passage 44, part of the fluid is jetted from nozzle 16, while the remainder is fed into chamber 74 through communication hole 75. As a result, slider 76 is moved away from the distal end face of tip 14, against the urging force of spring 77. Accordingly, backup plate 80 is moved toward the distal end face of tip 14. Thus, a calculus can be clamped between plate 80 and the distal end face of tip 14, to be held in a position facing nozzle 16. Backup plate 80, rod 78, and chamber 74 constitute retaining mechanism 64 for holding the calculus in position.

In the fifth and sixth embodiments described above, the calculus can be crushed securely by increasing the holding force of retaining mechanism 64, in conjunction with the pressure of the high-pressure fluid jetted from the nozzle, after the calculus is held by the retaining mechanism.

Figure 21:
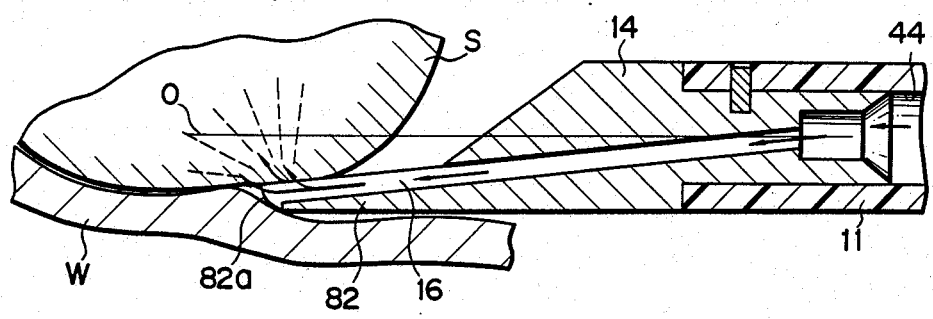
FIGS. 21 and 22 are a sectional view and a plan view, respectively, showing the distal end portion of a probe of a lithotomic apparatus according to a seventh embodiment of the invention.
Figure 22:
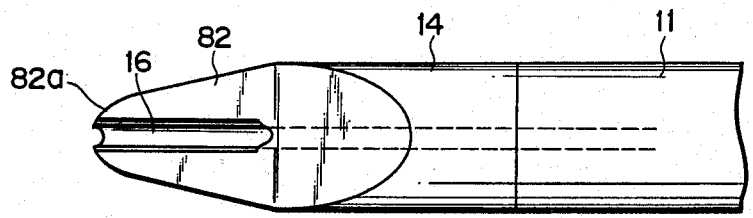

FIGS. 21 and 22 show a seventh embodiment of the present invention. A lithotomic apparatus according to this embodiment is adapted for separation of a calculus.

Probe 11 is composed of a tube whose inner peripheral surface defines feed passage 44. The proximal end of probe 11 is connected to the drive unit (FIG. 1), and distal tip 14 is fixed to the distal end of the probe. Tip 14 has flat lancet portion 82 protruding from its distal end face. The lancet portion is situated off or below the central axis of tip 14 or central axis 0 of probe 11. Projecting end 82a of lancet portion 82 has a smooth arcuate shape. Moreover, tip 14 is formed with nozzle 16 which extends along its axial direction. The rear end of nozzle 16 communicates with feed passage 44, while its front end portion opens to the upper surface and end 82a of lancet portion 82. Nozzle 16 reduces in circumference toward its front end.

In separating calculus S from body wall W by means of the lithotomic apparatus constructed in this manner, the distal end portion of lancet portion 82 is first placed at the junction between the calculus and the body wall. In this state, a high-pressure fluid is supplied pulsatively to feed passage 44 of probe 11 and then jetted from nozzle 16, by the drive unit. As a result, the fluid is dashed against calculus S, through that portion of nozzle 16 which opens to the upper surface of lancet portion 82. Thus, calculus S is separated from body wall W by the pressure of the high-pressure fluid.

According to the lithotomic apparatus described above, the distal end of the probe need not be forced in between the calculus and the body wall. Therefore, the calculus can be separated easily without injuring the body wall. Since the high-pressure fluid is jetted pulsatively, moreover, it is also prevented from injuring the body wall.

Figure 23:
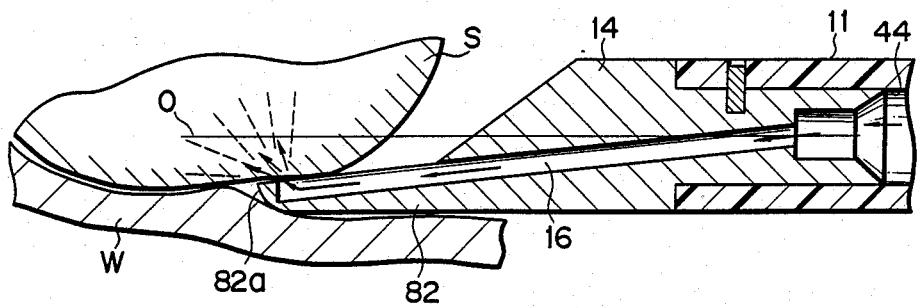
FIGS. 23 and 24 are a sectional view and a plan view, respectively, showing a first modification of the seventh embodiment.
Figure 24:
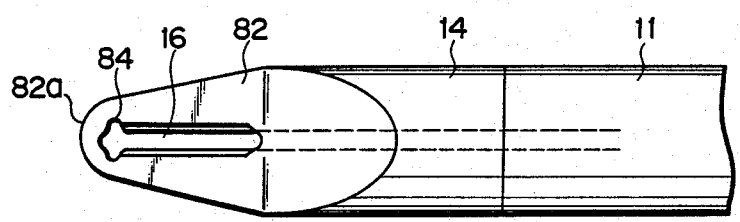

As is shown in FIGS. 23 and 24, nozzle 16 may be formed so as to communicate with groove 84 in lancet portion 82, instead of opening to projecting end 82a of the lancet portion. Groove 84, which is situated in a position somewhat recessed from end 82a toward the rear end of tip 14, opens to the upper surface of lancet portion 82, and extends at right angles to nozzle 16.

According to the aforementioned modification, the high-pressure fluid, jetted from nozzle 16, can spread sideways along groove 84, so that the area of calculus S to be subjected to the fluid jets can be increased, thus ensuring a more reliable separation.

Figure 25:
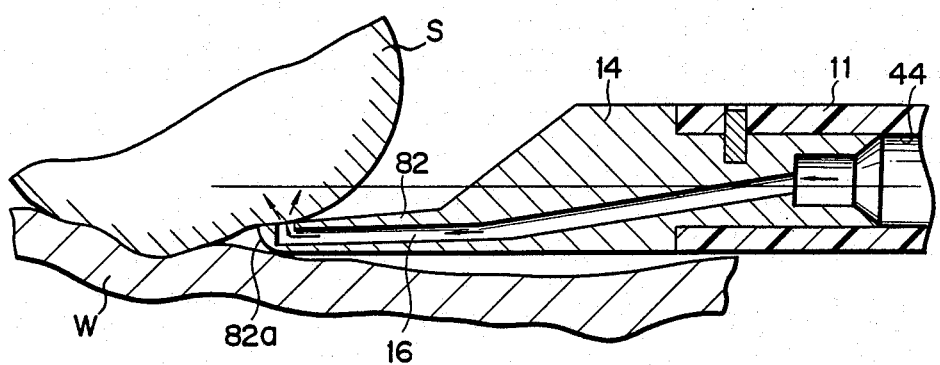

As is shown in FIGS. 25 and 26, moreover, nozzle 16 may be formed so that only its front end opens to the upper surface of lancet portion 82. In this case, the pressure of the high-pressure fluid, jetted from nozzle 16, is high enough to separate the calculus easily. The fluid can also be used to crush the calculus.

The shape of distal tip 14, fixed to the distal end of probe 11, is not limited to the one described in connection with the seventh embodiment, and may be changed as required.

For example, distal tip 14 may be formed with projections 86, as is shown in FIG. 27, or with recess 88, as is shown in FIG. 28. In such an arrangement, nozzle 16 in tip 14 cannot be brought into intimate contact with the calculus, so that the high-pressure fluid can be dashed efficiently against the calculus. As is shown in FIG. 29, moreover, nozzle 16 may be formed in the peripheral surface of tip 14, as well as in the distal end face thereof. Alternatively, slit- or cross-shaped groove 89 may be formed on the distal end face of tip 14, as is shown in FIG. 30 or 31, so that nozzle 16 opens to groove 89. As is shown in FIG. 32, groove 89 may be formed having a V-shaped cross section.

Figure 33:
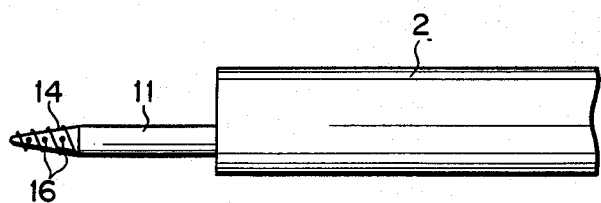
FIG. 33 is a side view showing a further modification of the distal tip.

As is shown in FIG. 33, furthermore, distal tip 14 may be in the form of a drill, having nozzles 16 opening to its peripheral surface. In this case, after a hole is made in the calculus by rotating tip 14, the high-pressure fluid is jetted from nozzles 16, with the tip kept in the hole.

Figure 34:
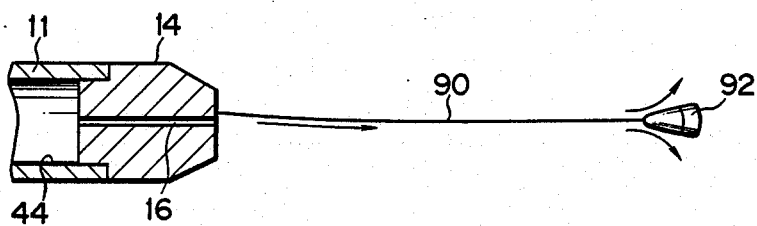
Figure 35:
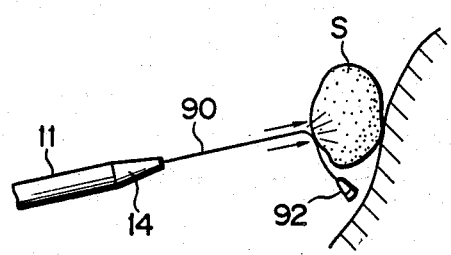

FIGS. 34 and 35 show an eighth embodiment of the present invention. In this embodiment, conical diffusion member 92 is coupled to distal tip 14 of probe 11 by means of fine wire 90 of a predetermined length. According to this arrangement, if a high-pressure fluid is jetted unexpectedly from probe 11, it flows along wire 90 and runs against the tapered surface of diffusion member 92, thereby scattering in all directions. Thus, the apparatus can be improved in safety. In crushing calculus S, if distal tip 14 of probe 11 is brought closer to the calculus, wire 90 bends so that diffusion member 92 is deflected from the passage of the fluid. As a result, calculus S can be crushed by means of the high-pressure fluid.

What is claimed is:

1. A lithotomic apparatus for treating a calculus produced in a body cavity, comprising:
    an elongated suction probe, that can be inserted into the body cavity, including a distal end, a proximal end, an inner tube defining an instrument channel having a distal end open to the distal end of the probe, an outer tube located around the inner tube with a gap therebetween, a suction channel defined between the inner and outer tubes and having an annular cross section, and a plurality of suction holes formed in the circumference of the outer tube to communicate with the suction channel and located near the distal end of the probe;
    suction means for sucking gas from the suction holes through the suction channel;
    an elongated viewing probe, that can be inserted into the instrument channel, for viewing a region near the distal end of the suction probe;
    an elongated treating probe, having a nozzle portion at a distal end thereof, that can be inserted into the instrument channel so that the nozzle portion projects from the distal end of the suction probe;
    means for supplying a high-pressure fluid; and
    a drive mechanism for feeding the high-pressure fluid to the treating probe and pulsatively ejecting the fluid from the nozzle portion, the drive mechanism including a control circuit for controlling the ejection of the fluid and the suction of the gas so that the pressure in a body cavity can be kept at a predetermined value.

2. An apparatus according to claim 1, wherein said drive mechanism includes adjusting means for adjusting the flow rate of the high-pressure fluid flowing through the communication means, and means for closing the communication means when the flow rate of the high-pressure fluid flowing through the communication means is higher than a level set by the adjusting means.

3. An apparatus according to claim 2, wherein said treating probe includes a feed passage communicating with the supply means and said nozzle portion includes a distal member fixed to the distal end of the treating probe, and a plurality of nozzles formed in the distal member and each having a proximal end communicating with the feed passage and a distal end opening to the distal end face of the distal member, said nozzles having their respective central axes and being formed so that the central axes intersect one another at a point at a predetermined distance from the distal member.

4. An apparatus according to claim 3, wherein each of said nozzles is reduced gradually in cross-sectional area with distance from the proximal end thereof.

5. An apparatus according to claim 1, wherein said drive mechanism includes communication means for connecting the supply means to the treating probe and permitting passage of the high-pressure fluid, and valve means arranged in the communication means, and said control circuit operates the valve means so as to open and close for a predetermined period and operate the suction means in accordance with the opening and closing of the valve means.

6. An apparatus according to claim 5, wherein said control circuit changes a capacity of the suction means so that a higher negative pressure is generated in the suction channel when the valve means is opened than when the valve means is closed.

7. A lithotomic apparatus for treating a calculus produced in a body cavity, comprising:
    an elongated suction probe, that can be inserted into the body cavity, including a distal channel having a distal end open to the distal end of the probe, an outer tube located around the inner tube with a gap therebetween, a suction channel defined between the inner and outer tubes and having an annular cross section, and a plurality of suction holes formed in the circumferences of the outer tube to communicate with the suction channel and located near the distal end of the probe;
    suction means for sucking gas from the suction holes through the suction channel;
    an elongated viewing probe, that can be inserted into the instrument channel, for viewing a region near the distal end of the suction probe;
    an elongated treating probe, having a nozzle portion at a distal end thereof, that can be inserted into the instrument channel so that the nozzle portion projects from the distal end of the suction probe;
    means for supplying a high-pressure fluid, and
    a drive means for feeding the high-pressure fluid to the treating probe and pulsatively ejecting the fluid from the nozzle portion.

* * * * *